(12) United States Patent
Skowron et al.

(10) Patent No.: US 10,874,735 B2
(45) Date of Patent: Dec. 29, 2020

(54) METHOD OF OBTAINING A POLYEPITOPIC PROTEIN AND POLYEPITOPIC DNA VECTOR

(71) Applicant: Bioventures Institute Sp. z o. o., Poznañ (PL)

(72) Inventors: Piotr Skowron, Gdansk (PL); Agnieszka Zylicz-Stachula, Gdansk (PL); Olga Zolnierkiewicz, Gdansk (PL); Malgorzata Skowron, Gdynia (PL); Lukasz Janus, Poznan (PL); Joanna Jezewska-Frackowiak, Gdansk (PL); Daria Krefft, Reda (PL); Dawid Nidzworski, Gdansk (PL); Kasjan Szemiako, Gdansk (PL); Natalia Maciejewska, Plosnica (PL); Marta Nowak, Reda (PL); Aneta Szymanska, Gdansk (PL)

(73) Assignee: BIOVENTURES INSTITUTE SP. Z O. O., Poznan (PL)

( * ) Notice: Subject to any disclaimer, the term of this patent is extended or adjusted under 35 U.S.C. 154(b) by 506 days.

(21) Appl. No.: 15/305,453

(22) PCT Filed: Apr. 21, 2015

(86) PCT No.: PCT/IB2015/052915
§ 371 (c)(1),
(2) Date: Oct. 20, 2016

(87) PCT Pub. No.: WO2015/162560
PCT Pub. Date: Oct. 29, 2015

(65) Prior Publication Data
US 2017/0095553 A1   Apr. 6, 2017

(30) Foreign Application Priority Data

Apr. 21, 2014  (PL) .......................... 407950

(51) Int. Cl.
| | |
|---|---|
| *C12N 15/66* | (2006.01) |
| *A61K 39/29* | (2006.01) |
| *C12N 15/64* | (2006.01) |
| *C12N 15/85* | (2006.01) |
| *C12N 15/10* | (2006.01) |
| *C07K 14/005* | (2006.01) |
| *C12N 15/70* | (2006.01) |
| *A61K 39/00* | (2006.01) |

(52) U.S. Cl.
CPC .......... *A61K 39/292* (2013.01); *C07K 14/005* (2013.01); *C12N 15/10* (2013.01); *C12N 15/64* (2013.01); *C12N 15/66* (2013.01); *C12N 15/70* (2013.01); *C12N 15/85* (2013.01); *A61K 2039/53* (2013.01); *A61K 2039/645* (2013.01); *C12N 2730/10122* (2013.01); *C12N 2730/10134* (2013.01); *C12N 2730/10151* (2013.01); *C12N 2800/80* (2013.01)

(58) Field of Classification Search
None
See application file for complete search history.

(56) References Cited

PUBLICATIONS

Sarrion-Perdigones A, Falconi EE, Zandalinas SI, Jua'rez P, Ferna'ndez-del-Carmen A, et al. (2011) GoldenBraid: An Iterative Cloning System for Standardized Assembly of Reusable Genetic Modules. PLoS ONE 6(7): e21622.*
Nian et al., 2008, Biotechnol Prog, vol. 24, pp. 417-425.*
Block et al., Methods in Enzymology, vol. 463, 2009, pp. 439-473.*
Willats, Plant Molecular Biology 50: 837-854, 2002.*
Lee et al., Genetic Analysis; Biomolecular Engineering, 1996, vol. 13, pp. 139-145.*
Gunther et al., Journal of Virology, 1995, vol. 69, pp. 5437-5444.*
Gunther et al., "A Novel Method for Efficient Amplication of Whole Hepatitis B Virus Genomes Permits Rapid Functional Analysis and Reveals Deletion Mutants in Immunosuppressed Patients," Journal of Virology (Jan. 1, 1995); 69(9):5437-5444.
Lee e tal., "Sequential amplification of cloned DNA as tandem multimers using class-IIS restriction enzymes," Genetic Analysis: Biomolecular Engineering (1996); 13:139-145.

* cited by examiner

*Primary Examiner* — Mindy G Brown
(74) *Attorney, Agent, or Firm* — Fox Rothschild LLP

(57) ABSTRACT

The present invention is directed to a method of manufacturing a polyepitopic protein comprising the steps of cloning a blunt-ended DNA sequence by encoding the epitope that is to be cloned into a DNA vector recognized by the endonuclease SmaI or the endonuclease SapI and isolating the polyepitopic protein by transforming a bacterial host cell with such vector.

14 Claims, 10 Drawing Sheets
Specification includes a Sequence Listing.

```
     3    6    9    12   15   18   21
     |    |    |    |    |    |    |
    ACC  Aaa  CCG  ACC  GAC  CGT  AAC      (SEQ ID NO: 9)
    Thr  Lys  Pro  Thr  Asp  Gly  Asn      (SEQ ID NO: 10)
```

FIG. 3

12-mer of a 5-mer concatemer from the 1st round of HBV epitope amplification (+ 3-nt sticky end DNA)

M  K  5'  10'  20'  40'  80'  160'  MIX  M 1500 pz 1000 pz 500 pz 100 pz

Fig. 6

SEQUENCE LISTING

```
<160> NUMBER OF SEQ ID NOS: 27

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence: Synthetic
      pAMP1-A: amplifying module

<400> SEQUENCE: 1
```

```
atgcgctctt cacccgggcc cagaagagct aagtaagtaa g                    41
```

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      pAMP1-B: amplifying module

<400> SEQUENCE: 2

```
atggctcttc acccgggccc agaagagcta agtaagtaag                      40
```

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
      pAMP1-C: amplifying module

<400> SEQUENCE: 3

```
atgccgctct tcacccgggc cagaagagc taagtaagta ag                    42
```

<210> SEQ ID NO 4
<211> LENGTH: 59
<212> TYPE: DNA
<213> ORGANISM: Artificial Sequence
<220> FEATURE:
<223> OTHER INFORMATION: Description of Artificial Sequence: Synthetic
      pAMP1-HisA: amplifying module

<400> SEQUENCE: 4

```
atgcaccacc accaccacca cagctcttca cccgggccca gaagagctaa gtaagtaag   59
```

<210> SEQ ID NO 5
<211> LENGTH: 58
<212> TYPE: DNA
<213> ORGANISM: Artificial Sequence
<220> FEATURE:
<223> OTHER INFORMATION: Description of Artificial Sequence: Synthetic
      pAMP1-HisB: amplifying module

<400> SEQUENCE: 5

```
atgcaccacc accaccacca cgctcttcac ccgggcccag aagagctaag taagtaag    58
```

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      pAMP1-HisC: amplifying module

<400> SEQUENCE: 6

```
atgcaccacc accaccacca cccgctcttc acccgggccc agaagagcta agtaagtaag  60
```

<210> SEQ ID NO 7
<211> LENGTH: 3003
<212> TYPE: DNA
<213> ORGANISM: Artificial Sequence
<220> FEATURE:
<223> OTHER INFORMATION: Description of Artificial Sequence: Synthetic
      vector pAMP1-HisA

<400> SEQUENCE: 7

```
catgcaccac caccaccacc acagctcttc acccgggccc agaagagcta agtaagtaag  60
```

```
agctcgaccc ggtcgaattt gctttcgaat ttctgccatt catccgctta ttatcactta    120
ttcaggcgta gcaccaggcg tttaagggca ccaataactg ccttaaaaaa attacgcccc    180
gccctgccac tcatcgcagt actgttgtaa ttcattaagc attctgccga catggaagcc    240
atcacagacg gcatgatgaa cctgaatcgc cagcggcatc agcaccttgt cgccttgcgt    300
ataatatttg cccatggtga aaacgggggc gaagaagttg tccatattgg ccacgtttaa    360
atcaaaactg gtgaaactca cccagggatt ggctgagacg aaaaacatat tctcaataaa    420
ccctttaggg aaataggcca ggttttcacc gtaacacgcc acatcttgcg aatatatgtg    480
tagaaactgc cggaaatcgt cgtggtattc actccagagc gatgaaaacg tttcagtttg    540
ctcatggaaa acggtgtaac aagggtgaac actatcccat atcaccagct caccgtcttt    600
cattgccata cggaattccg gatgagcatt catcaggcgg gcaagaatgt gaataaaggc    660
cggataaaac ttgtgcttat ttttctttac ggtctttaaa aaggccgtaa tatccagctg    720
aacggtctgg ttataggtac attgagcaac tgactgaaat gcctcaaaat gttctttacg    780
atgccattgg gatatatcaa cggtggtata tccagtgatt ttttctcca ttttagcttc     840 cttagctcct gaaaatctcg ataactcaaa aaatacgccc ggtagtgatc ttatttcatt    900
atggtgaaag ttggaacctc ttacgtgccg atcaacgtct cattttcgcc aaaagttggc    960
ccagggcttc ccggtatcaa cagggacacc aggattatt tattctgcga agtgatcttc    1020
cgtcacaggt atttattcgg cgcaaagtgc gtcgggtgat gctgccaact tactgattta    1080
gtgtatgatg gtgttttga ggtgctccag tggcttctgt ttctatcagc tgtccctcct    1140
gttcagctac tgacggggtg gtgcgtaacg gcaaaagcac cgccggacat cagcgctagc    1200
ggagtgtata ctggcttact atgttggcac tgatgagggt gtcagtgaag tgcttcatgt    1260
ggcaggagaa aaaaggctgc accggtgcgt cagcagaata tgtgatacag gatatattcc    1320
gcttcctcgc tcactgactc gctacgctcg gtcgttcgac tgcggcgagc ggaaatggct    1380
tacgaacggg gcggagattt cctggaagat gccaggaaga tacttaacag ggaagtgaga    1440
gggccgcggc aaagccgttt ttccataggc tccgcccccc tgacaagcat cacgaaatct    1500
gacgctcaaa tcagtggtgg cgaaacccga caggactata aagataccag gcgtttcccc    1560
ctggcggctc cctcgtgcgc tctcctgttc ctgcctttcg gtttaccggt gtcattccgc    1620
tgttatggcc gcgtttgtct cattccacgc ctgacactca gttccgggta ggcagttcgc    1680
tccaagctgg actgtatgca cgaaccccc gttcagtccg accgctgcgc cttatccggt     1740
aactatcgtc ttgagtccaa cccggaaaga catgcaaaag caccactggc agcagccact    1800
ggtaattgat ttagaggagt tagtcttgaa gtcatgcgcc ggttaaggct aaactgaaag    1860
gacaagtttt ggtgactgcg ctcctccaag ccagttacct cggttcaaag agttggtagc    1920
tcagagaacc ttcgaaaaac cgccctgcaa ggcggttttt tcgttttcag agcaagagat    1980
tacgcgcaga ccaaaacgat ctcaagaaga tcatcttatt aatcagataa aatatttcta    2040
gatttcagtg caatttatct cttcaaatgt agcacctgaa gtcagcccca tacgatataa    2100
gttgtaattc tcatgtttga cagcatgcca tcgatcgcga tcttgctcaa ttgttatcag    2160
ctatgcgccg accagaacac cttgccgatc agccaaacgt ctcttcaggc cactgactag    2220
cgataacttt ccccacaacg gaacaactct cattgcatgg gatcattggg tactgtgggt    2280
ttagtggttg taaaaacacc tgaccgctat ccctgatcag tttcttgaag gtaaactcat    2340
cacccccaag tctggctatg cagaaaatca cctggctcaa cagcctgctca gggtcaacga    2400
```

-continued

```
gaattaacat tccgtcagga aagcttggct tggagcctgt tggtgcggtc atggaattac    2460
cttcaacctc aagccagaat gcagaatcac tggcttttt ggttgtgctt acccatctct    2520
ccgcatcacc tttggtaaag gttctaagct caggtgagaa catccctgcc tgaacatgag    2580
aaaaaacagg gtactcatac tcacttctaa gtgacggctg catactaacc gcttcataca    2640
tctcgtagat ttctctggcg attgaagggc taaattcttc aacgctaact ttgagaattt    2700
ttgcaagcaa tgcggcgtta taagcattta atgcattgat gccattaaat aaagcaccaa    2760
cgcctgactg ccccatcccc atcttgtctg cgacagattc ctgggataag ccaagttcat    2820 tttctttt ttcataaatt gctttaaggc gacgtgcgtc ctcaagctgc tcttgtgtta    2880
atggtttctt ttttgtgctc atacgttaaa tctatcaccg caagggataa atatctaaca    2940
ccgtgcgtgt tgactatttt acctctggcg gtgataatgg ttgcatgtac taaggaggtt    3000
gtt                                                                 3003
```

<210> SEQ ID NO 8
<211> LENGTH: 3348
<212> TYPE: DNA
<213> ORGANISM: Artificial Sequence
<220> FEATURE:
<223> OTHER INFORMATION: Description of Artificial Sequence: Synthetic
      vector pAMP1-HisA-13-epitope

<400> SEQUENCE: 8

```
catgcaccac caccaccacc acagctcttc acccaccaaa ccgaccgacg gtaacgggcc     60
caccaaaccg accgacggta acgggcccac caaaccgacc gacggtaacg ggcccaccaa    120
accgaccgac ggtaacgggc ccaccaaacc gaccgacggt aacgggccca ccaaaccgac    180
cgacggtaac gggcccacca aaccgaccga cggtaacggg cccaccaaac cgaccgacgg    240
taacgggccc accaaaccga ccgacggtaa cgggcccacc aaaccgaccg acggtaacgg    300
gcccaccaaa ccgaccgacg gtaacgggcc caccaaaccg accgacggta acgggcccac    360
caaaccgacc gacggtaacg ggcccagaag agctaagtaa gtaagagctc gacccggtcg    420
aatttgcttt cgaatttctg ccattcatcc gcttattatc acttattcag gcgtagcacc    480
aggcgtttaa gggcaccaat aactgcctta aaaaaattac gccccgccct gccactcatc    540
gcagtactgt tgtaattcat taagcattct gccgacatgg aagccatcac agacggcatg    600
atgaacctga atcgccagcg gcatcagcac cttgtcgcct tgcgtataat atttgcccat    660
ggtgaaaacg ggggcgaaga agttgtccat attggccacg tttaaatcaa actggtgaa    720 actcacccag ggattggctg agacgaaaaa catattctca ataaacctt tagggaaata    780 ggccaggttt tcaccgtaac acgccacatc ttgcgaatat atgtgtagaa actgccggaa    840
atcgtcgtgg tattcactcc agagcgatga aaacgtttca gtttgctcat ggaaaacggt    900
gtaacaaggg tgaacactat cccatatcac cagctcaccg tctttcattg ccatacggaa    960
ttccggatga gcattcatca ggcgggcaag aatgtgaata aaggccggat aaaacttgtg    1020 cttattttc tttacggtct ttaaaaaggc cgtaatatcc agctgaacgg tctggttata    1080
ggtacattga gcaactgact gaaatgcctc aaaatgttct ttacgatgcc attgggatat    1140
atcaacggtg gtatatccag tgatttttt ctccatttta gcttccttag ctcctgaaaa    1200
tctcgataac tcaaaaata cgcccggtag tgatcttatt tcattatggt gaaagttgga    1260
acctcttacg tgccgatcaa cgtctcattt tcgccaaaag ttggcccagg cttcccggt    1320 atcaacaggg acaccaggat ttattttatc tgcgaagtga tcttccgtca caggtattta    1380
```

-continued

```
ttcggcgcaa agtgcgtcgg gtgatgctgc caacttactg atttagtgta tgatggtgtt    1440
tttgaggtgc tccagtggct tctgtttcta tcagctgtcc ctcctgttca gctactgacg    1500
gggtggtgcg taacggcaaa agcaccgccg acatcagcg ctagcggagt gtatactggc    1560
ttactatgtt ggcactgatg agggtgtcag tgaagtgctt catgtggcag agaaaaaag    1620
gctgcaccgg tgcgtcagca gaatatgtga tacaggatat attccgcttc ctcgctcact    1680
gactcgctac gctcggtcgt tcgactgcgg cgagcgaaa tggcttacga acggggcgga    1740
gatttcctgg aagatgccag gaagatactt aacagggaag tgagagggcc gcggcaaagc    1800
cgttttccca taggctccgc ccccctgaca agcatcacga atctgacgc tcaaatcagt    1860
ggtggcgaaa cccgacagga ctataaagat accaggcgtt tcccctggc ggctccctcg    1920
tgcgctctcc tgttcctgcc tttcggttta ccggtgtcat tccgctgtta tggccgcgtt    1980
tgtctcattc cacgcctgac actcagttcc gggtaggcag ttcgctccaa gctggactgt    2040
atgcacgaac ccccgttca gtccgaccgc tgcgccttat ccggtaacta tcgtcttgag    2100
tccaacccgg aaagacatgc aaaagcacca ctggcagcag ccactggtaa ttgatttaga    2160
ggagttagtc ttgaagtcat gcgccggtta aggctaaact gaaaggacaa gttttggtga    2220
ctgcgctcct ccaagccagt tacctcggtt caaagagttg gtagctcaga gaaccttcga    2280
aaaaccgccc tgcaaggcgg tttttttcgtt ttcagagcaa gagattacgc gcagaccaaa    2340
acgatctcaa gaagatcatc ttattaatca gataaaatat ttctagattt cagtgcaatt    2400
tatctcttca aatgtagcac ctgaagtcag ccccatacga tataagttgt aattctcatg    2460
tttgacagca tgccatcgat cgcgatcttg ctcaattgtt atcagctatg cgccgaccag    2520
aacaccttgc cgatcagcca aacgtctctt caggccactg actagcgata actttcccca    2580
caacggaaca actctcattg catgggatca ttgggtactg tgggtttagt ggttgtaaaa    2640
acacctgacc gctatccctg atcagtttct tgaaggtaaa ctcatcaccc ccaagtctgg    2700
ctatgcagaa atcacctggc tcaacagcct gctcagggtc aacgagaatt aacattccgt    2760
caggaaagct tggcttggag cctgttggtg cggtcatgga attccttca acctcaagcc    2820
agaatgcaga atcactggct tttttggttg tgcttaccca tctctccgca tcacctttgg    2880
taaaggttct aagctcaggt gagaacatcc ctgcctgaac atgagaaaaa acagggtact    2940
catactcact tctaagtgac ggctgcatac taaccgcttc atacatctcg tagatttctc    3000
tggcgattga agggctaaat tcttcaacgc taactttgag aattttttgca agcaatgcgg    3060
cgttataagc atttaatgca ttgatgccat taaataaagc accaacgcct gactgcccca    3120
tccccatctt gtctgcgaca gattcctggg ataagccaag ttcattttc tttttttcat    3180
aaattgcttt aaggcgacgt gcgtcctcaa gctgctcttg tgttaatggt ttcttttttg    3240
tgctcatacg ttaaatctat caccgcaagg gataaatatc taacaccgtg cgtgttgact    3300
attttacctc tggcggtgat aatggttgca tgtactaagg aggttgtt                 3348
```

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      sequence encoding the HBV epitope
<220> FEATURE:
<221> NAME/KEY: CDS
<222> LOCATION: (1)..(21)

<400> SEQUENCE: 9

```
acc aaa ccg acc gac ggt aac                                          21
Thr Lys Pro Thr Asp Gly Asn
1               5
```

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      sequence encoding the HBV epitope

<400> SEQUENCE: 10

```
Thr Lys Pro Thr Asp Gly Asn
1               5
```

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      Amplifying module

<400> SEQUENCE: 11

```
gctcttcacc cgggcccaga agagc                                          25
```

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Synthetic
      pAMP1-A upper oligo

<400> SEQUENCE: 12

```
catgcgctct tcacccgggc ccagaagagc taagtaagta ag                       42
```

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Synthetic
      pAMP1-A lower oligo

<400> SEQUENCE: 13

```
agctcttact tacttagctc ttctgggccc gggtgaagag cg                       42
```

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence: Synthetic
      pAMP1-HisA upper oligo

<400> SEQUENCE: 14

```
catgcaccac caccaccacc acagctcttc acccgggccc agaagagcta agtaagtaag    60
```

<210> SEQ ID NO 15
<211> LENGTH: 60
<212> TYPE: DNA
<213> ORGANISM: Artificial Sequence
<220> FEATURE:
<223> OTHER INFORMATION: Description of Artificial Sequence: Synthetic
      pAMP1-HisA lower oligo

<400> SEQUENCE: 15
agctcttact tacttagctc ttctgggccc gggtgaagag ctgtggtggt ggtggtggtg    60

<210> SEQ ID NO 16
<211> LENGTH: 182
<212> TYPE: DNA
<213> ORGANISM: Artificial Sequence
<220> FEATURE:
<223> OTHER INFORMATION: Description of Artificial Sequence: Synthetic
      PCR sequence containing the insert (variant with 5 HBV
      antigen repeats) for the Phage Display System

<400> SEQUENCE: 16
caccaccacc acaggaattc acccaccaaa ccgaccgacg gtaacgggcc caccaaaccg    60
accgacggta acgggcccac caaaccgacc gacggtaacg ggcccaccaa accgaccgac   120
ggtaacgggc ccaccaaacc gaccgacggt aactaagctt gaagagctaa gtaagtaaga   180
gc                                                                 182

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      Top primer for the Phage Display System

<400> SEQUENCE: 17
caccaccacc acaggaattc acccacca                                      28

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
      Bottom primer for the Phage Display System

<400> SEQUENCE: 18
gctcttactt acttagctct tcaagcttag ttaccgtcg                          39

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Arg Ser Ser Pro
1               5

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Ala Leu His
1

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met Pro Leu Phe Thr
1               5

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met His His His His His His Ser Ser Ser Pro
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met His His His His His His Ala Leu His
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met His His His His His His Pro Leu Phe Thr
1               5                   10

<210> SEQ ID NO 25
<211> LENGTH: 220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
aggaggttgt tcatgcacca ccaccaccac cacagctctt cacccaccaa accgaccgac      60
ggtaacgggc ccaccaaacc gaccgacggt aacgggccca ccaaaccgac cgacggtaac     120
gggcccacca aaccgaccga cggtaacggg cccaccaaac cgaccgacgg taacgggccc     180
agaagagcta agtaagtaag agctcgaccc ggtcgaattt                           220

<210> SEQ ID NO 26
<211> LENGTH: 60
<212> TYPE: PRT

-continued

```
<213> ORGANISM: Artificial Sequence
<220> FEATURE:
<223> OTHER INFORMATION: Description of Artificial Sequence: Synthetic
      polypeptide

<400> SEQUENCE: 26

Met His His His His His His Ser Ser Ser Pro Thr Lys Pro Thr Asp
1               5                   10                  15

Gly Asn Gly Pro Thr Lys Pro Thr Asp Gly Asn Gly Pro Thr Lys Pro
                20                  25                  30

Thr Asp Gly Asn Gly Pro Thr Lys Pro Thr Asp Gly Asn Gly Pro Thr
            35                  40                  45

Lys Pro Thr Asp Gly Asn Gly Pro Arg Arg Ala Lys
        50                  55                  60

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 27

His His His His His His
1               5
```

METHOD OF OBTAINING A POLYEPITOPIC PROTEIN AND POLYEPITOPIC DNA VECTOR

CROSS-REFERENCE TO RELATED APPLICATIONS

This application is a U.S. National Phase of International Application No. PCT/IB2015/052915, filed Apr. 21, 2015, which claims priority to Poland Application No. P. 407950, filed Apr. 21, 2014, the content of which are incorporated herein by reference.

FIELD OF INVENTION

The subject of the present invention is a method of obtaining a polyepitopic protein as well as a DNA vector for embodying this method. The proteins obtained according to the present invention protein may find a number of uses, and in particular for the production of improved vaccines.

DESCRIPTION OF RELATED ART

Shen, S-H *P.N.A. Sci USA* 81:4627-4631 (1984) discloses a method of obtaining of a multimeric proinsulin (up to 7 copies). The multimers were obtained using the consecutive concatenation of DNA lengths using synthetic DNA fragments cut with the IIS endonuclease SfaNI, alkaline phosphatase, polynucleotide kinase and DNA ligase. This method, however, did not make it possible to produce a multiply repeated DNA sequence in one reaction, because each time only a single additional monomer copy could be added.

Lennick et al. *Gene* 61:103-112 (1987) discloses multimeric gene encoding 8 copies of a peptide hormone—atrial natriuretic peptide. The method described does not use a vector that would make it possible to generate multiple copies of sequences encoding a peptide, and the resulting multimeric gene produced in vitro was finally cloned into a commonly used expression vector. This method also has not made it possible to easily multiply the DNA sequence in a single reaction, because each time a only single additional monomer copy could be added.

Kim, S. C. and Szybalski, W., *Gene* 71:1-8 (1988) discloses a method of directionally amplifying a cloned DNA fragment using a IIS restriction endonuclease—BspM1, the pSK3 DNA vector as well as DNA ligase. 30 monomer copies were obtained in the concatemer. However, the use of BspM1 is made difficult in practice, because it does not digest the substrate DNA completely. In effect, it's not possible to maintain ORF continuity, and the amplification introduces additional DNA sequences into the amplified concatemer. The method described does not make it possible to repeat the amplification cycle which significantly limits the possibility of obtaining the desired number of repeating DNA segments. The vector disclosed was not an expression vector.

Lee, J. H. et al., *Genetic Analysis: Biomolecular Engineering* 13:139-145 (1996) discloses a method of directionally amplifying a cloned DNA fragment sing the IIS restriction endonucleases BspM1 and Bbsl, the pBBS1 DNA vector as well as DNA ligase. This method, based on the autoligation of 4-nucleotide (nt) sticky DNA ends makes it impossible to maintain ORF continuity, since it made it possible to repeat the amplification cycle in order to achieve the desired number of copies of the amplified DNA segment. The vector used was not an expression vector. The method was used to amplify a short antibacterial peptide gene—mogainin (108 copies).

Lee, J. H. et al., *Protein Expression and purification* 12:53-60 (1998) discloses another variant of a method based on the previously described vector, pBBS1. The vector used was not an expression vector. The authors used the Bbsl enzyme to generate 4-nt sticky ends, seriously impeding ORF continuity. The document describes the production of no more than 6 copies of the DNA monomer DNA in the amplified sequence. The method was used for amplifying the mogainin antibacterial peptide gene as well as bufferin II.

Wang, Y.-Q and Cai, J. Y. *Appl Biochem Biotechnol.* 141:203-13 (2007) discloses another variant of multimerizing genes encoding antibiotic peptides using the autoligation of synthetic DNA fragments, containing asymmetric sticky ends in the presence of 2 DNA adapters. The adapters contained sequences recognised by the restriction endonucleases Sall and EcoRl. The procedure used no vector, the amplification is hard to control and requires the addition of consecutive portions of the synthetic DNA monomer during the reaction. The disclosed method of polymeric gene construction, designed for the production of antibacterial peptides, resulted in 8 monomer copies in a polymeric protein.

BRIEF SUMMARY OF THE INVENTION

The goal of the present invention is to deliver a method of easily obtaining a polyepitopic protein of arbitrary length, a vector useful in the embodiment of the method as well as of obtaining higher order polyepitope structures. The resulting polyepitopic proteins as well as higher order polyepitope structures are useful in a broad selection of uses, and in particular can be used to produce improved vaccines of increased efficacy.

The subject of the present invention is a DNA vector containing the sequence of the amplifying module encompassing two convergent DNA sequences recognised by the Sapl endonuclease and the intervening DNA sequence containing the site for the cloning-in of the insert recognised by the endonuclease Smal, wherein preferably the amplifying module possesses the sequence GCTCTT-CACCCGGGCCCAGAAGAGC (Seq. Id. No. 11).

Preferably, a DNA vector according to the present invention is a protein expression vector, which additionally contains an origin of replication, preferably p15A, antibiotic resistance gene, preferably chloramphenicol, a transcription promoter, preferably PR of the lambda bacteriophage, a repressor gene, preferably c1857ts, a translation initiation signal, and possibly a sequence encoding 6 histidine residues, as well as a sequence encoding a translation stop signal.

Preferably, a DNA vector according to the present invention contains a sequence selected from amongst sequences 1-6 also shown in FIG. 2.

Preferably, a DNA vector according to the present invention possesses sequence 7 (pAMP1-HisA).

The next the subject of the present invention is a method of obtaining a polyepitopic protein characterised in that:

a) a blunt-ended DNA sequence encoding the epitope is cloned into a DNA vector defined above at a site recognised by the endonuclease Smal or a sticky-ended DNA sequence encoding the epitope is cloned into a DNA vector defined above at a site recognised by the Sapl endonuclease. Optionally, in order to increase concatamer formation efficiency, it is possible to carry out a pre-ligation of the DNA sequence with sticky ends, which ensure directional ligation prior to adding the vector that had been SapI-digested.

b) the resulting vector is amplified in bacterial host, isolated and digested with the IIS subtype restriction SapI endonuclease, and then the isolated fragment containing the DNA sequence encoding the epitope, modified such that, it is equipped with single-stranded sticky ends, that ensure the directional ligation of the insert to the concatemer, c) the isolated fragment is autoligated, d) the autoligation product is cloned into a DNA vector defined in claims 1-4 at a site recognised by the subtype IIS restriction SapI endonuclease and e) the resulting vector is used to transform a bacterial host and ant then the polyepitopic protein is expressed and isolated, wherein in order to increase the size of the polyepitopic protein, stages from b) to d) are repeated prior to realising stage e).

Optionally, use is made of another epitope amplification stage by immobilizing the resulting polyepitopic protein defined above on a macromolecular carrier, such as: microorganisms, cells, bacteria, bacteriophages, viruses, defective virions, autoaggregating proteins, or nanoparticles.

BRIEF DESCRIPTION OF THE DRAWINGS

FIG. 3. Depicts a model 7 amino-acid epitope of the HBV surface antigen subjected to the amplification reaction.

FIG. 6. Provides the results of the second round of amplification of a pentamer concatemer of the HBV epitope.

DETAILED DESCRIPTION OF THE INVENTION

The following examples contain a detailed description of one possible embodiment variant of the method according to the present invention. An alternative method of cloning in the insert is the use of a SapI-digested vector with sticky ends filled in using DNA polymerase in the presence of deoxyribonucleotide triphosphates. Following the present invention a person skilled in the art can propose subsequent embodiment variants.

Preferably, the epitope is a HBV epitope, particularly that encoded by the synthetic sequence 9 (see also FIG. 3).

Figure 1:
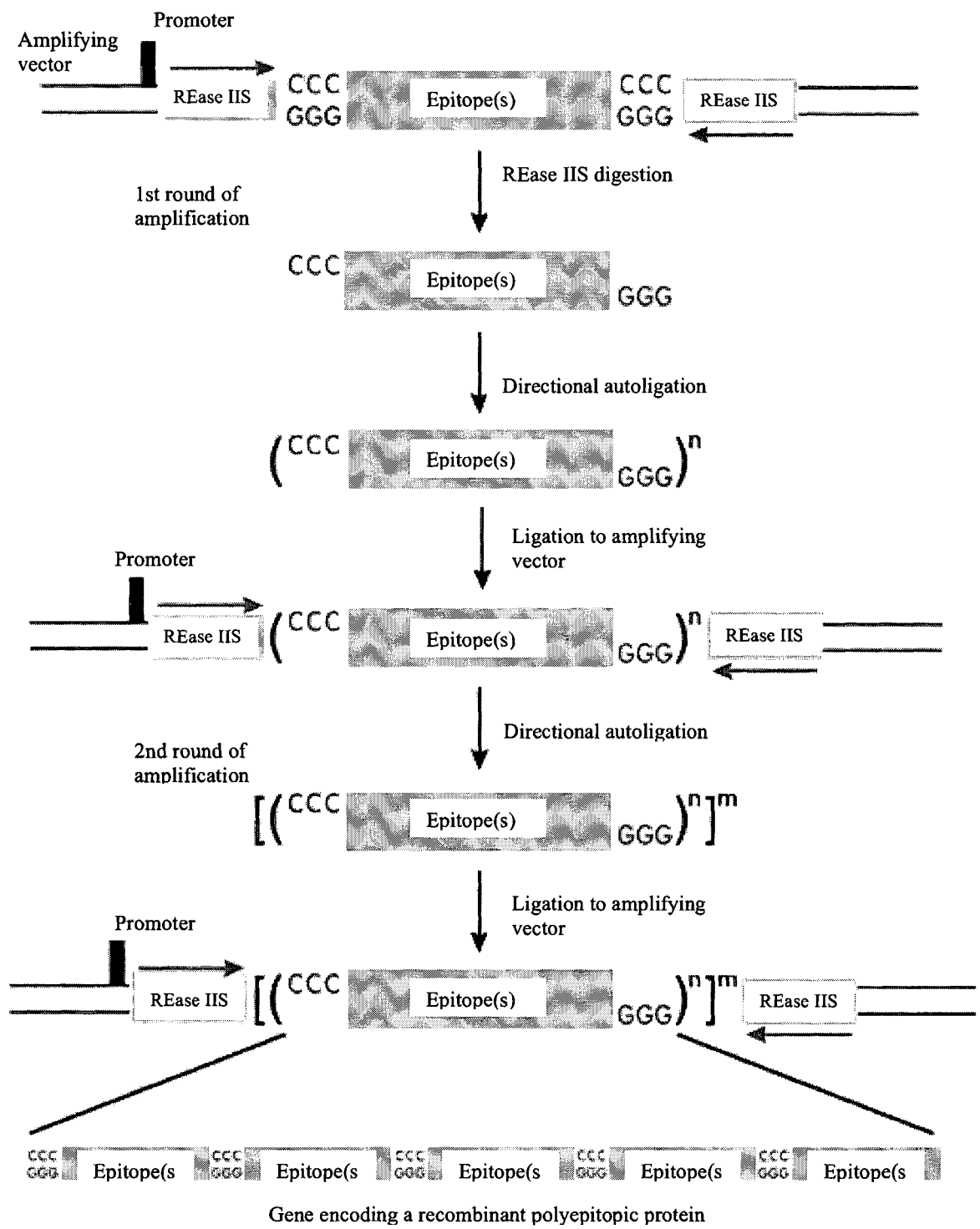
FIG. 1. Illustrates a general schematic of the method according to the present invention described using the example of the amplification of the surface antigen of HBV. This represents a schematic of the amplification vector as well as amplification reaction of the epitope (in the figure: synthetic HBV epitope).

Preferably, the amplified monomer segment may contain different epitopes, from different proteins or different regions of the same protein, preferably encoded by a synthetic sequence (see schematic in FIG. 1).

We also disclose a method of constructing as well as using artificial genes that do not occur in nature using genetic engineering methods as well as chemical synthesis, containing multiple DNA copies encoding repeating segments, containing multiple monomer units of one or more peptides. The amplification of a gene, encoding a peptide (epitope) with a particular biological or chemical function leads to the amplification of the desirable interaction of the resulting (poly)peptide with a specific ligand. In particular such polyepitopic proteins are useful as: (i) artificial antigens—a new generation of vaccines with a magnified potential stimulation of the immune system; (ii) polyproteins containing modules for rare metal chelation for their industrial production or environmental remediation; (iii) a binding module for enzyme cofactors (such as cations, anions, organic molecules) such as proteases acting within a wound in order to stop deleterious activities; (iv) protective multi-epitopic proteins, multiplex modules containing peptides with activators or inhibitors of biological functions for the treatment of molecular, viral and bacterial diseases; (V) multiepitopic proteins containing multimers of peptide hormones or biologically active fragments of signalling proteins and those that stimulate tissue regeneration. Such proteins, placed in a wound, would gradually release biologically active peptides under the influence of proteinases, stimulating the regeneration of tissue; (vi) the polyepitopic protein is immobilized on macromolecular carriers, such as: microorganisms, cells, bacteria, bacteriophages, viruses, defective virions, autoaggregating proteins, or nanoparticles. The immobilization may be performed using genetic or chemical means. Immobilized polyepitopic proteins, may magnify the effect of the envisaged uses (i)-(vi).

In particular, we designed a vector-enzymatic system for the amplification of a DNA segment. The amplified DNA segment may be natural origin or the result of a chemical synthesis.

Example 1. General Schematic of the Embodiment of the Method According to the Present Invention FIG. 1 illustrates a general schematic of the method according to the present invention described using the example of the amplification of the surface antigen of HBV. This represents a schematic of the amplification vector as well as amplification reaction of the epitope (in the figure: synthetic HBV epitope).

The amplifying vector contains 2 convergent DNA sequences recognised by the sub-type IIS restriction endonuclease, that preferentially recognises a relatively long DNA sequence, which cuts DNA and generates 3-nt (or multiples of 3 nt) sticky ends. We used the SapIendonuclease, whose particular characteristic is that it recognises a relatively long sequence of 7 base pairs (unique in the vector and amplified DNA segment) which cuts DNA at a distance of 1 nt in the upper chain and 4 nt in the lower chain, thereby generating 3-nt sticky ends, or the equivalent of a single codon. The SapI sites are adjacent in the vector to the sequence of the classic Type II endonuclease, which is designed for cloning in the inserted DNA. We used the SmaI endonuclease, which cuts DNA within the recognition sequence, generating the so-called "blunt" ends. A vector cut with SmaI may be cloned with any arbitrary DNA segment, synthetic or natural, which is then to be amplified. In a preferable embodiment, the amplified DNA segment encodes an antigen or amino-acid sequence encompassing several identical or differing antigens. The only limit is the length of the amplified fragment, as dictated by the length of the insert DNA accepted by a given class of DNA vector. The amplifying module may be transferred to different classes of vectors using cloning.

Example 2. A Series of 6 Designed pAMP1 Vectors

Figure 2:
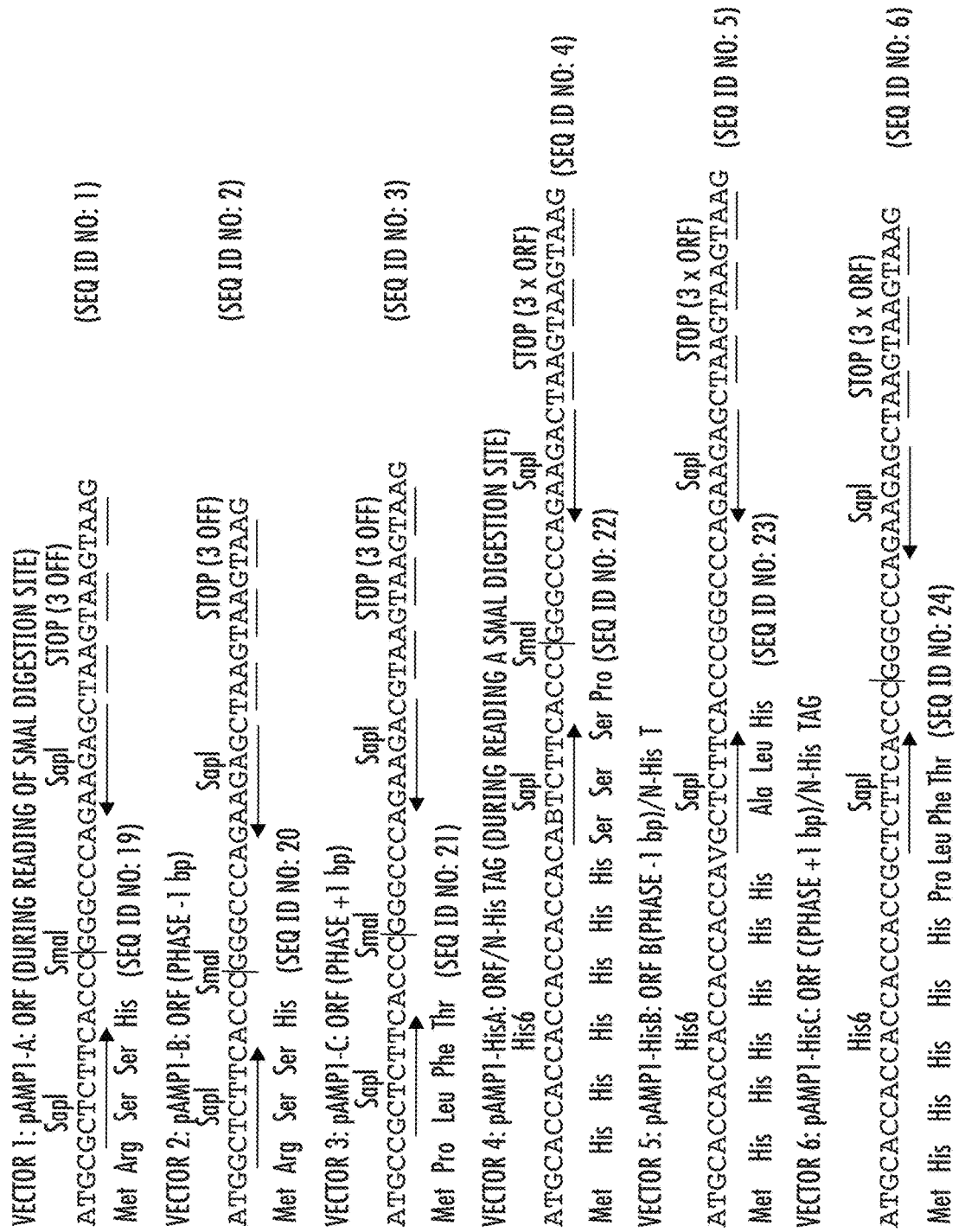
FIG. 2. Depicts the designed the 1st series of pAMP vectors, based on the pACYC184 vector skeleton. Vectors contain the origin of replication p15A, an antibiotic resistance gene against chloramphenicol, the strong transcription promoter PR from the lambda bacteriophage, a repressor gene, cI857ts, translation initiation signals, a sequence of 6 histidine residues with an affinity for nickel ions, a restriction site system for fusing to the translation start codon ATG as well as a module for the directional amplification of a DNA fragment maintaining the ORF, containing convergent restriction sites for a IIS subtype endonuclease SapI.

In the example embodiment shown in FIG. 2 we designed the 1st series of pAMP vectors, based on the vector skeleton, containing a p15A origin of replication. From among the designed vectors, we built pAMP1-A (not containing the 6 histidine residue fusion tag) as well as pAMP1-HisA (containing the 6 histidine residue tag). Additionally, the pAMP vector series was built with the option of the high expression of proteins under the control of the lambda phage PR as well as the option of fusing with the His6 tag, which enables the isolation of the polyepitopic protein using an efficient metalloaffinity chromatography protocol.

Vectors contain the origin of replication p15A, an antibiotic resistance gene against chloramphenicol, the strong transcription promoter PR from the lambda bacteriophage, a repressor gene, c1857ts, translation initiation signals, a sequence of 6 histidine residues with an affinity for nickel ions, a restriction site system for fusing to the translation start codon ATG as well as a module for the directional amplification of a DNA fragment maintaining the ORF, containing convergent restriction sites for a IIS subtype endonuclease, preferably SapI, separated by a short DNA segment, which can contain ancillary restriction sites for cloning in the insert DNA, preferably SmaI. The variants differ in terms of the possibility of manipulating three reading frames (which may be significant when amplifying natural, non-synthetic DNA sequences) as well as the presence or absence of a His6 tag (excellent for easing the subsequent isolation of the expressed polyepitopic protein, regardless of its charge, solubility and other biochemical parameters). Variant 4 was used for the following example of the amplification of the epitope from the surface antigen of HBV. The amplifying module may be introduced by way of cloning in various classes of vector, containing, for example, alternative origins of replication, antibiotic resistance genes, transcriptional promoters and translation signals. For example, we transferred the amplifying module to the vector pBAD/Myc-HisA as well as pET21d21d(+), possessing ampicillin resistance, a colE1 origin of replication as well as araBAD or T7 transcription promoters, respectively. Synthetic modules with sticky ends for the enzymes NcoI and SacI, in versions containing and not containing the His6 residue affinity tag, were cloned into a vector cut with these enzymes, thereby enabling the expression of the polyepitopic proteins using the araBAD or T7 promoters (respectively). We obtained the vectors: pBADAMP1-A, pBAD-AMP1-HisA, pETAMP1-A, pETAMP1-HisA possessing the inserted amplifying module at the standard MCS (multiple cloning site).

Figure 8:
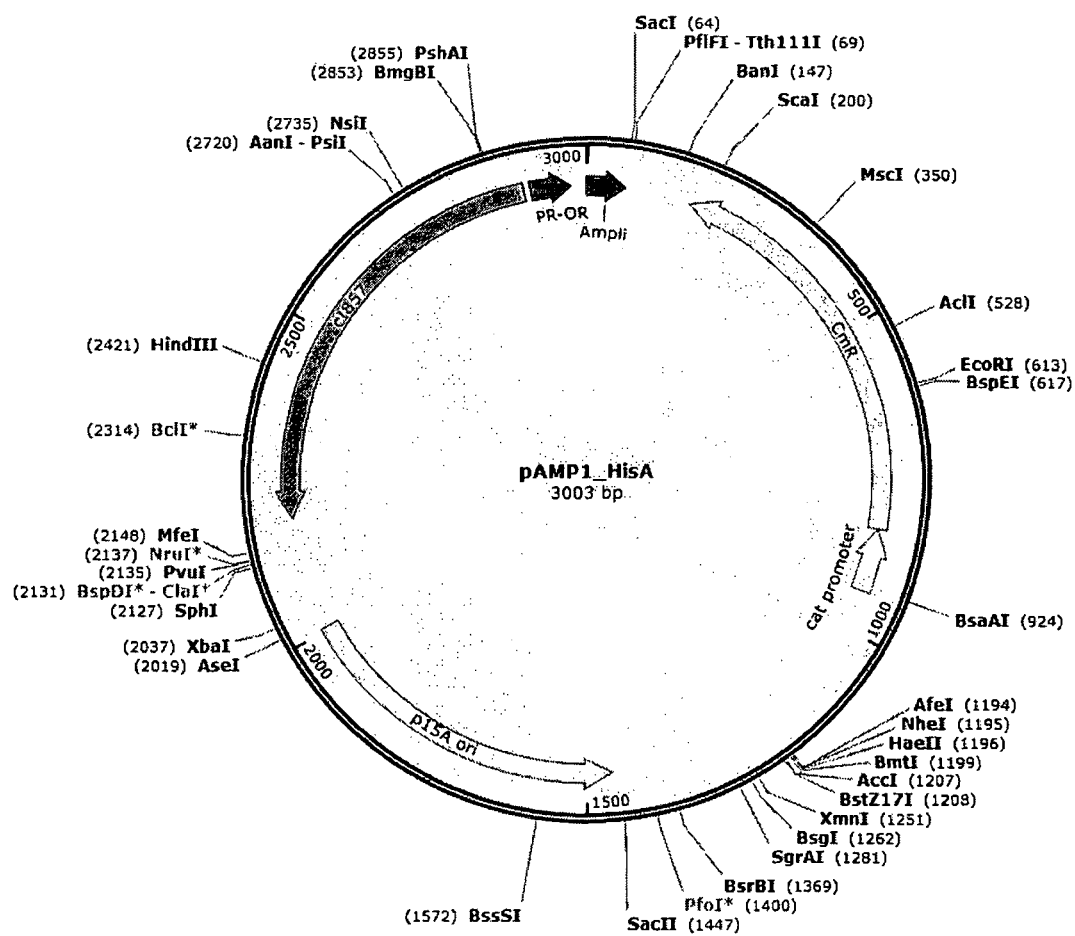
FIG. 8. Provides the genetic map of the amplification-expression vector pAMP1-HisA vector.
Figure 9:
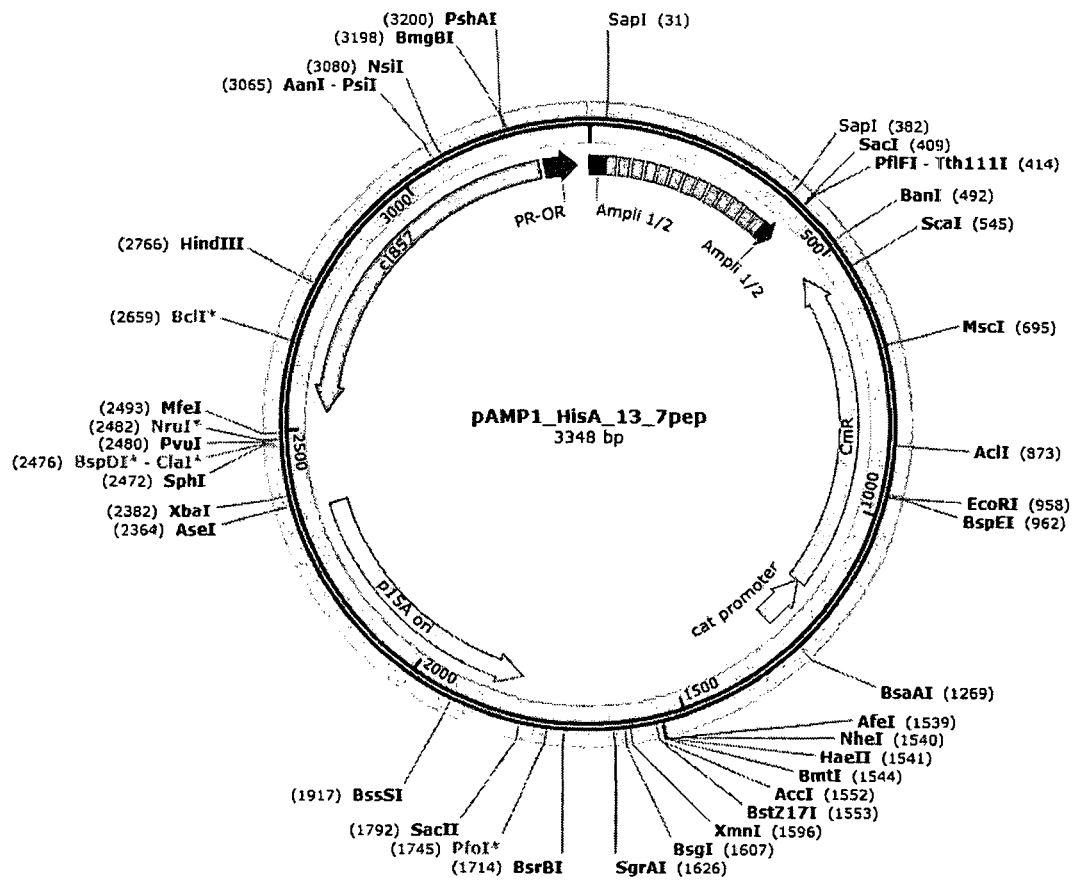
FIG. 9. Provides the genetic map of the expression vector pAMP1_HisA_13_7_pep, containing a variant of the 13-copy concatemer gen resulting from the amplification of a 7-amino-acid epitope of HBV, where each epitope is separated by a proline residue.

The full sequence of the pAMP1-HisA vector used in example 3 is shown as sequence 7. Furthermore, in FIG. 8 we show a restriction map of the pAMP1-HisA vector, and in FIG. 9 a restriction map of the pAMP1-HisA vector with a cloned-in 13-mer antigenic peptide.

The sequences of the synthetic oligodeoxyribonucleotides, encoding the amplifying module transferred into pBAD and pET vectors, used in example 2 are shown as sequences 12, 13, 14 and 15.

Example 3. Production of a Polyepitopic Protein Containing a Model 7 Amino-Acid Epitope of the HBV Surface Antigen A model 7 amino-acid epitope of the HBV surface antigen subjected to the amplification reaction is shown in FIG. 3.

The synthetic DNA fragment encoding the epitope of the HBV surface antigen was subjected to a pilot amplification experiment in the vector pAMP1-HisA. We obtained >60 copies of the epitope in the DNA concatemer in vitro as well as 13 copies IN THE HYBRID polyepitopic protein cloned in vivo.

Figure 4:
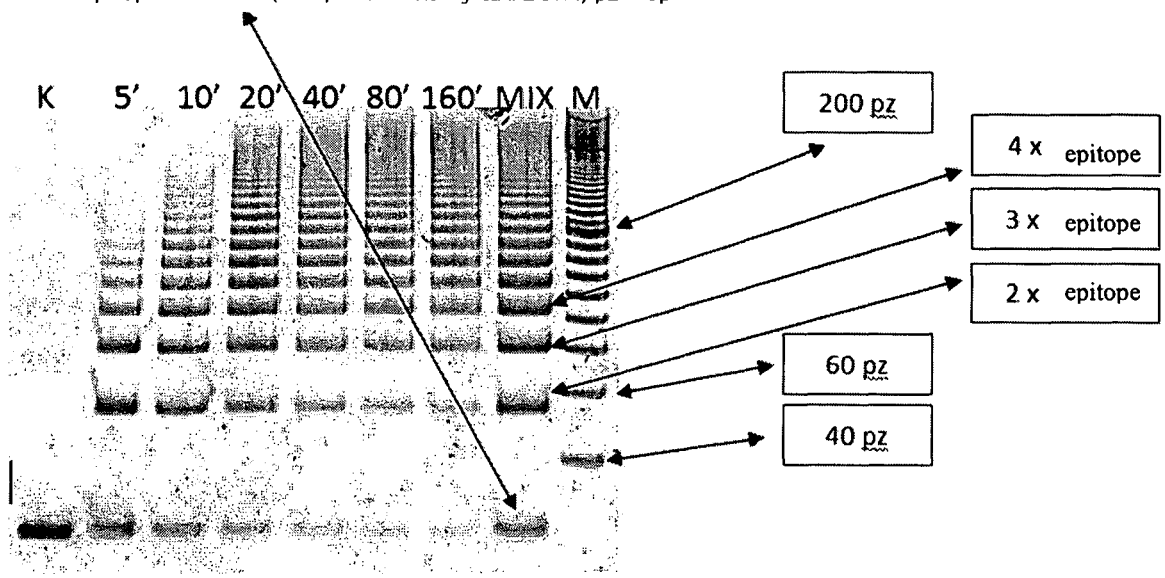
FIG. 4. Provides the results of the amplification reaction in vitro of a 7 amino-acid epitope from the model HBV surface protein using the pAMP1-HisA vector, the SapI endonuclease as well as DNA ligase.

FIG. 4 shows the results of the amplification reaction in vitro of a 7 amino-acid epitope from the model HBV surface protein using the pAMP1-HisA vector, the SapI endonuclease as well as DNA ligase.

We analysed the amplification reaction using PAGE. We cloned a synthetic DNA fragment of 21 bp into the amplifying vector pAMP1-HisA, encoding the 7 amino-acid epitope of HBV. A plasmid containing the monomer HBV epitope digested with the SapI endonuclease, excising the modified epitope gene from the plasmid construct. The modification consisted of adding to it 3-nt, single-stranded 5' sticky ends. Aside from the amplification function, in the final polymeric hybrid protein, these ends are responsible for the addition of a proline residue, the so-called "helical breaker", which separate the epitope monomers and facilitate the independent folding of the epitope into tertiary structures, thereby help to maintain their natural spatial structure. The number of added "helical breakers" can be regulated arbitrarily by incorporating amino-acids encoding them to the end of the synthetic epitope (at the level of its encoding DNA). The excised modified DNA encoding the epitope was subjected to autoligation in vitro. Lanes from 5 to 160 minutes show the autoligation kinetics. Reaction products were analysed electrophoretically, yielding a series of DNA segments of increasing length, that are directional concatemers (polymers) of the epitope gene in relation to the control reaction without the DNA ligase (K). The resulting in vitro concatemers were re-cloned into pAMP1-HisA, where they could be subjected to another amplification cycle or expression of the encoded multimeric protein.

Figure 5:
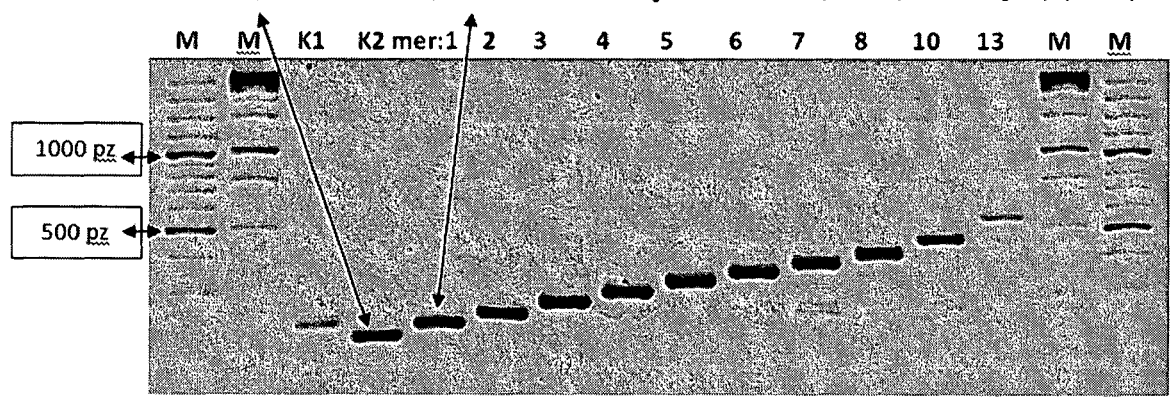
FIG. 5. Provides the results of hybrid clone analysis of genes encoding the polyepitope HBV protein obtained during the first amplification round.

FIG. 5 shows the results of hybrid clone analysis of genes encoding the polyepitope HBV protein obtained during the first amplification round.

The mixture of in vitro polymerised synthetic HBV epitope genes (FIG. 4, lane: MIX) using the following system: the amplification vector pAMP1-HisA/Sapl endonuclease/DNA ligase was recloned into the amplification vector pAMP1-HisA, so as to fix the variants of poly-HBV epitope genes, express the encoded polyepitopic proteins as well as to reiterate the amplification cycle. In the first round of the amplification reaction, we obtained a series of clones, containing from 2 to 13 copies of the epitope (lanes 1-13, PCR analysis, DNA fragments migrate slower and slower due to their increasing length, a direct sign of the number of attached epitope copies). An analysis of the DNA sequence showed the continuity of the ORF in the resulting constructs, thus each such synthetic poly-gene encodes different polyepitopic HBV protein, which is significant in terms of the target role of these synthetic proteins. This is due to the fact that their different variants will induce differing intensities of immune response as well as differing in solubility. After re-excising with Sapl, each of the concatemer gene variants may be in completely subjected to another amplification reaction, leading to subsequent poly-genes composed of hundreds of copies of the HBV epitope gene (separated by proline residues), within the hybrid construct, maintaining ORF continuity in an *Escherichia coli* bacterial hyperexpression system. Thereby, each consecutive amplification round increases the number of monomer copies in the concatemer at a geometric rate, leading in a short time to obtaining the planned number of copies in the target plasmid construct variants.

FIG. 6 shows the results of the second round of amplification of a pentamer concatemer of the HBV epitope.

The DNA fragment was excised using the Sapl endonuclease from a pAMP1-HisA construct containing a concatemer of 5 epitope copies, obtained during the 1st round of amplification and subjected to amplification again. The largest concatemer, visible at the edge of agarose gel resolution, contains 12 copies of the pentamer, constituting a 60-fold directionally polymerised HBV epitope. Larger concatemers are evidently visible, although not separated into distinct bands. The resulting 2nd round products were recloned into pAMP-HisA and may be subjected to a third round of round of amplification, leading to the production of hundreds or thousands of HBV epitope copies, set out in a single recombinant polypeptide (protein) with a continuous ORF. These clones were also subjected to analytical expression in order to obtain variants of epitope multiplication within the polyepitopic protein.

Figure 7:
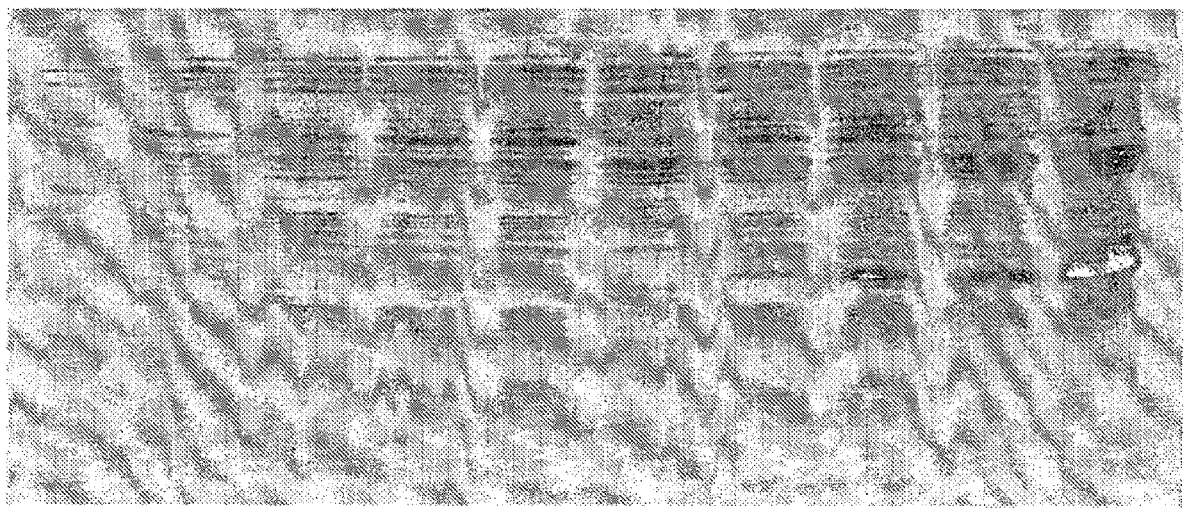
FIG. 7. Depicts an example expression of the hybrid gene encoding the polyepitopic HBV protein, obtained during the first round of amplification (13-mer) in the pAMP1-HisA vector. The results show electrophoretic analysis of the expressed polyHBV epitope 13-mer in a polyacrylamide gel under denaturing conditions and Coomassie Blue staining.

FIG. 7 shows an example expression analysis of the hybrid gene encoding the polyepitopic HBV protein, obtained during the first, model, round of amplification (13-mer) in the pAMP1-HisA vector (Seq. Id. No. 7, FIG. 8). We performed an electrophoretic analysis of the expressed polyHBV epitope 13-mer in a polyacrylamide gel under denaturing conditions and Coomassie Blue staining. Lane M, protein mass marker (GE LMW Calibration Kit); lanes KO-3: recombinant *Escherichia coli* culture, containing a 13-mer HBV construct prior to induction, and sampled at 0, 1, 2 and 3 hours. lanes 1 h-16 h: recombinant *Escherichia coli* cultures, containing the 13-mer HBV construct after thermal induction, sampled at 1, 2, 3, 4 and 16 hours. The red arrow indicates the growing HBV 13-mer band, stained purple-red. The unusual purple-red staining of the 13-mer band, whose concentration increases over the duration of the expression induction in bacteria (consecutive lanes), stems from the ordered arrangement of the stain on repeating sequence amino-acid segments and may thus serve as an additional tests for the presence of polyepitopic proteins during detection and isolation. We used expression analysis (protein synthesis in vivo) on a clone containing a variant of the 13-copy concatemer genu resulting from the amplification of a 7-amino-acid epitope of HBV, where each epitope is separated by a proline residue (expression plasmid see: Seq. Id. No. 8, FIG. 9). This technology maintains ORF continuity. The expression was conducted in the system: *Escherichia coli* I PR lambda bacteriophage promoter, yielding the over-expression of the artificial polyepitopic HBV protein.

Figure 10:
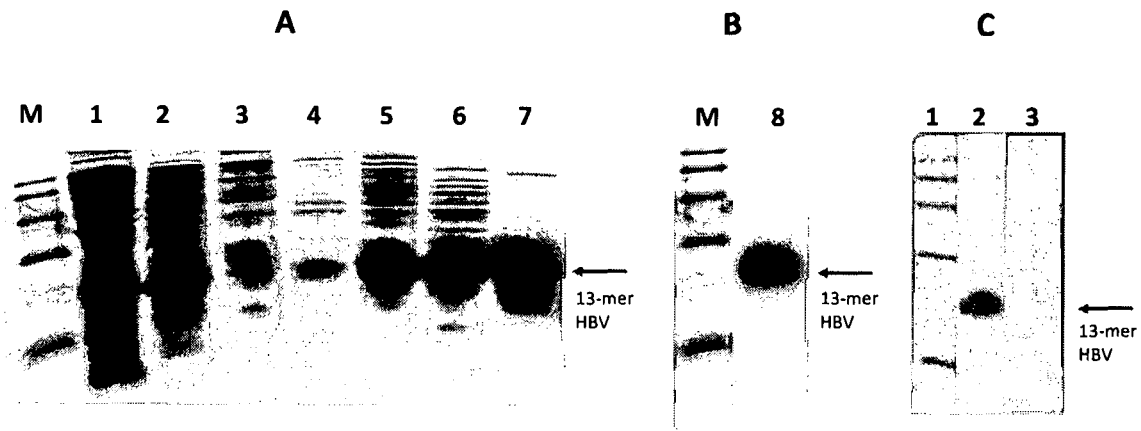
FIG. 10. Provides the isolation procedure of the expression of the polyepitopic protein example variant: 13-copy concatemer gene and Western blot detection.
Figure 11:
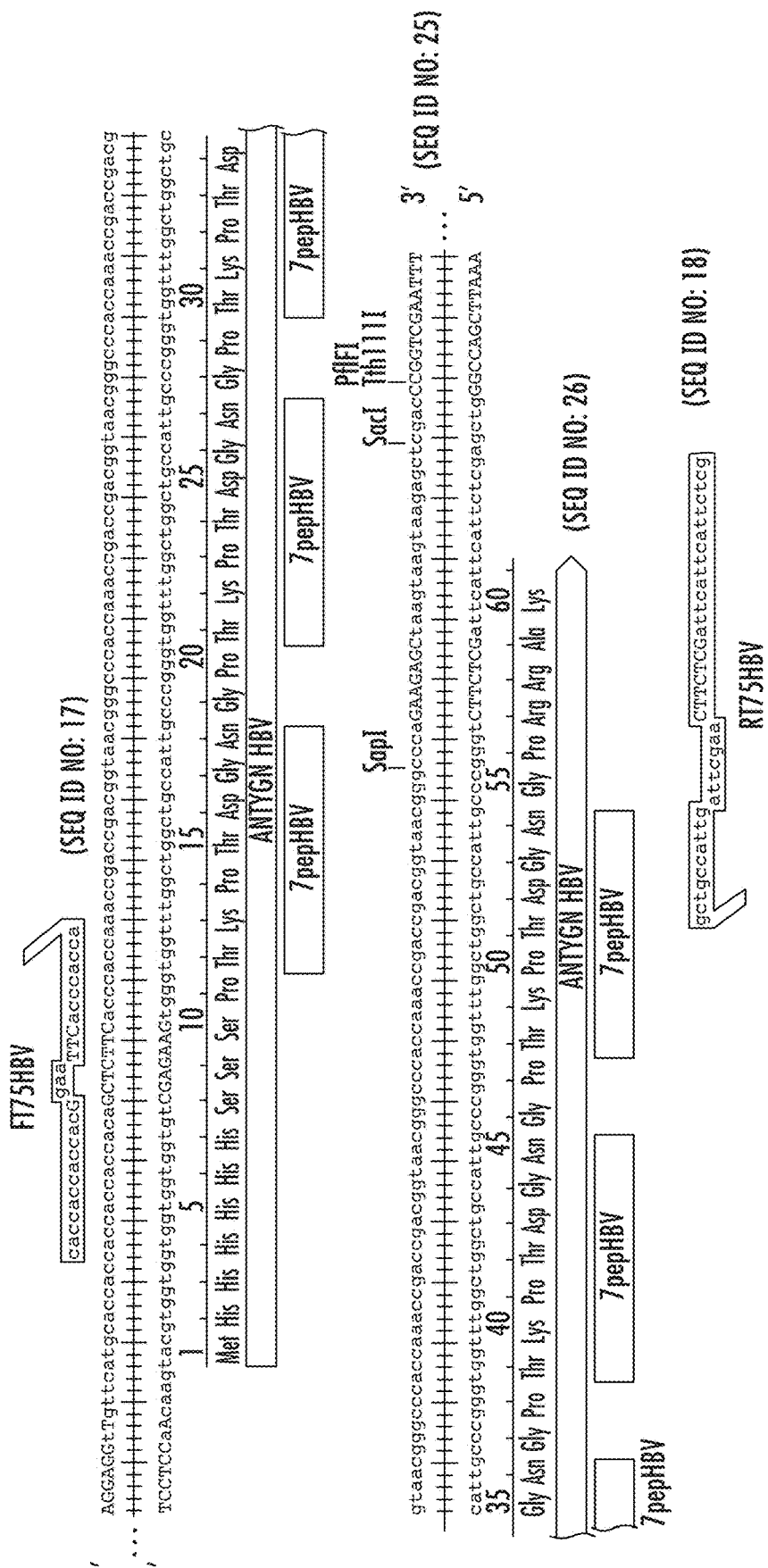
FIG. 11. Provides for the sequence of a poly-genic polyepitopic protein of a pentamer epitope with indicated primers that serve to amplify the HBV epitope polygene and to introduce the restriction sites for EcoRI and HindIII, which are used for genetically fusing it with a bacteriophage vector.
Figure 12:
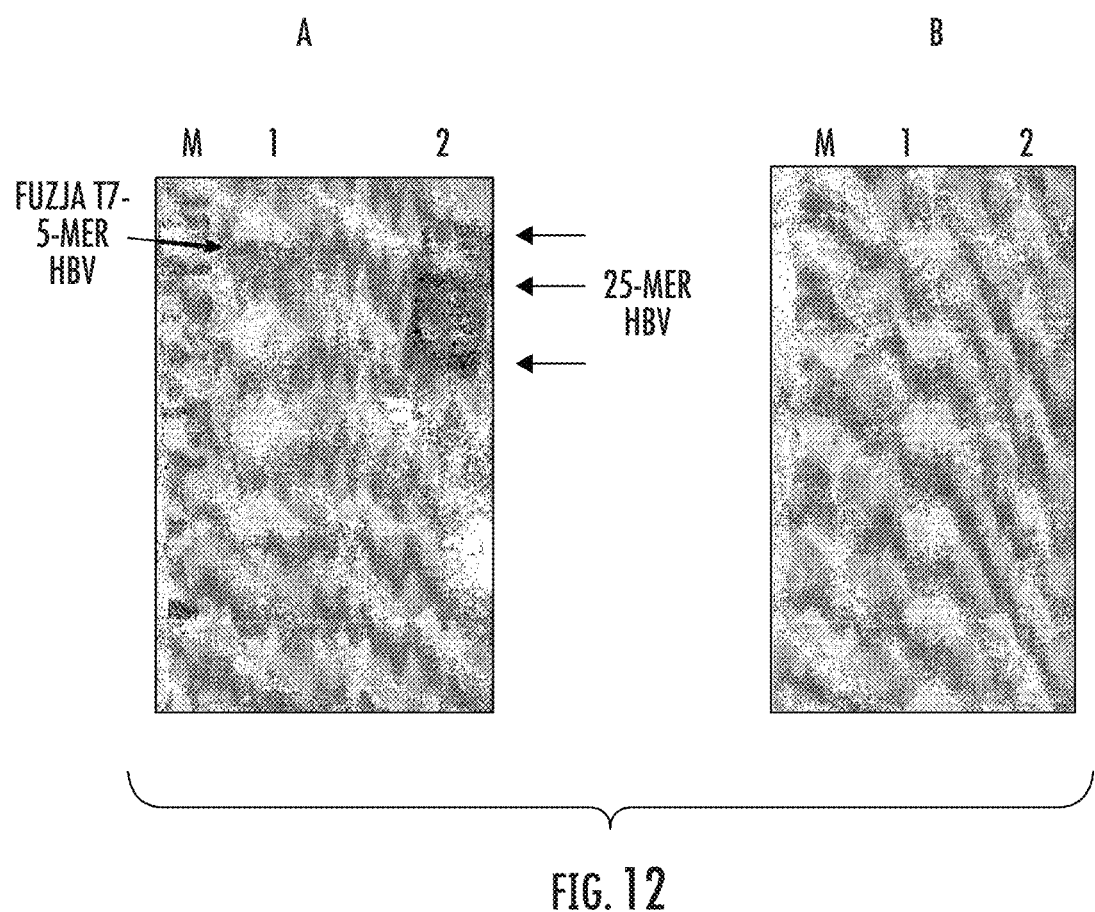
FIG. 12. Depicts the western blot of a purified 25-copy HBC epitope concatemer and recombinant T7 bacteriophage displaying several hundred copies of the pentamer HBV epitope.

FIG. 10 ABC represents the isolation procedure of the expression of the polyepitopic protein example variant: 13-copy concatemer gene, as well as Western blot detection. From a preparative (10 L) recombinant bacterial culture (bearing the amplification vector, expressing the 13-mer HBV epitope) and after induction and expression, w centrifuged off the bacterial biomass and subjected it to the following procedures: (i) ultrasonic disintegration and centrifugation of cellular debris; (ii) heating the lysate to 65° C. to denature the host proteins and centrifugation of the precipitated proteins; (iii) treatment of the preparation with buffered polyethylenimine in order to remove nucleic acids as well as acidic host proteins and centrifugation of the precipitate; (iv) fractioning by salting out with ammonium sulphate, centrifuging the precipitate containing the 13-mer HBV epitope and its dissolution in a buffer for use in a subsequent isolation stage; (v) AKTA high-performance affinity chromatography in a gel for chelating nickel ions— HiTrap IMAC HP, which binds the 6 histidine residue tag at the N-end of the 13-mer; (vi) AKTA high-performance molecular sieving chromatography in Superdex 200 pg. The purified preparation of the electrophoretically homogenous 13-mer polyepitopic protein was subjected to Western blotting using anti-6 histidine residue tag monoclonal antibodies, where the chromogenic reaction was performed using conjugated HRP as well as 3,3',4,4'-tetraaminobiphenyl tetrahydrochloride. FIG. 10 shows: panels A-B: denaturing PAGE of samples from consecutive stages of isolating the 13-mer HBV epitope. Lane: M—molecular mass marker (GE LMW Calibration Kit); lane 1—recombinant bacteria cells expressing the 13-mer; lane 2—cell extract resulting from ultrasonication; lane 3—denatured protein precipitate after heating; lane 4—supernatant containing the 13-mer after treatment with polyethylenimine; lane 5 and 6—supernatant containing 13-mer after fractionation with ammonium sulphate; lane 7—HBV 13-mer after purification using metalloaffinity chromatography; lane 8—homogenous 13-mer after molecular sieving chromatography; panel C: Western blot detection. Lane 1—molecular mass marker (GE LMW Calibration Kit); lane 2—purified HBV 13-mer preparation; lane 3—Western blot detection with anti-6 histidine residue tag (Merck) antibodies.

Because none of the recombinant host's own proteins contain the sequence of 6 histidines, the positive reaction indisputably confirms that the isolated protein is the polyepitope 13-mer of HBV. An additional confirmation is the expected size of the isolated protein in comparison to mass markers as well as specific binding to the HiTrap IMAC HP gel. The procedure is universal, successfully confirmed in the isolation of other variants of polyepitopic proteins, fused with 6 histidine residue tags, and contains varying amounts of polymerised HBV epitope.

Example 4. Production of Higher Order Multimeric Structures Containing Several Hundred Immobilised Copies of the Polyepitopic Protein, Containing the Model 7 Amino-Acid Epitope of the HBV Surface Antigen on the Capsid Surface of T7 Bacteriophage The construction of polyepitopic proteins facilitates a multiple increase in the concentration of the epitope in a single protein molecule, and a subsequent amplification stage is based on the combination of many polyepitopic protein molecules in one higher order structure. This may be achieved: (i) biologically, through the fusion of the gene encoding the polyepitopic protein with the genetic material of a higher order structural carrier such as a chromosome, nucleoid, microorgamal plasmid, a bacterium, bacteriophage or virus or (ii) by chemical means, through the use of factors that conjoin macromolecules.

FIG. 11 represents the sequence of a poly-genic poly-epitopic protein of a pentamer epitope with indicated primers that serve to amplify the HBV epitope polygene and to introduce the restriction sites for EcoRI and HindIII, which are used for genetically fusing it with a bacteriophage vector. This sequence was used to design an example biological immobilisation procedure for the polyepitope HBV pentamer epitope protein on the surface of the T7 bacteriophage capsid which infects *Escherichia coli*. We used the commercial Novagen T7Select® Phage Display System in the version using the phage vector T7Select415-1b. The system precisely immobilised 415 polypeptide copies with a length not exceeding ca. 50 amino-acid residues, thus the complete macromolecular structure, where we preferably used a pentamer HBV epitope, contains 2075 copies HBV epitope. The immobilisation procedure for the polyepitopic protein on the bacteriophage capsid surface consists of the following stages: (i) PCR amplification of the fragment encoding the pentamer HBV epitope, introducing restriction sites for the endonucleases HindIII and EcoRI, dedicated for the vector T7Select415-1 b for cloning DNA fragments, while maintaining ORF continuity for its translation with a protein forming the T7 capsid; (ii) digestion of the PCR-amplified fragment with the restriction endonucleases HindIII and EcoRI; (iii) directional ligation of the digested PCR fragment with pre-digested HindIII and EcoRI left and right arms of the T7 bacteriophage; (iv) packing in vitro of the recombinant T7 bacteriophage and infection of the host *Escherichia coli*; (v) isolation of individual clones of the recombinant T7 bacteriophage, amplification of the clones as well as validation of the DNA sequence produced with the designed sequence.

The sequence of the PCR product being the substrate for producing the insert for the Phage Display System (encoding a variant of the pentamer HBV epitope) used in Example 4 is shown as sequence 16, and the sequences of the PCR primers used to amplify the variant of 5 HBV epitopes are shown as sequences 17 and 18.

Example 5. Immunological Activity of the Polyepitope HBV Protein

The 25-mer polyepitope HBV protein of Example 2 was isolated from recombinant bacteria using the procedure shown in Example 4. Representative groups of mice (6 individuals each) were inoculated with 20 ug/mouse with a purified 25-mer in PBS buffer mixed with Freund's incomplete adjuvant. In parallel, we inoculated a control group with PBS and Freund's incomplete adjuvant. The vaccination cycle encompassed 3 injections at 3-week intervals.

FIG. 12 shows a Western blot of a purified 25-mer used in example 3 as well as a recombinant T7 bacteriophage displaying several hundred copies of the pentamer HBV epitope used in example 4. The samples, separated using denaturing PAGE, were Western blotted, using sera from mice inoculated with the 25-mer polyepitope HBV protein mixed with incomplete Freund's adjuvant as well as the sera of control mice inoculated with PBS and incomplete Freund's adjuvant. Lane M, Page Ruler marker; lane 1, purified recombinant bacteriophage containing the pentamer HBV epitope. Panel A left-hand arrow denotes the position of the fusion protein of the bacteriophage T7 capsid and the pentamer HBV epitope. The right-hand arrows in Panel A show multimeric forms of the purified 25-mer protein; Lane 2: 25-mer polyepitope HBV protein according to FIG. 10 purified to homogeneity. The results show a specific humoral immune response after 3 initial immunisation cycles, directed against multimers of the 7-amino-acid HBV epitope, present both in the polyepitopic protein as well as polyepitopic proteins displayed on the capsid of the recombinant bacteriophage T7. At the same time, a positive Western blot result, in addition to the DNA sequence of the recombinant bacteriophage T7, validates the correctness of the Example 4 cloning procedure and the variants of recombinant bacteriophages displaying the pentamer HBV epitope, as well as indicating the possibility of using the described technology in variants of new generation vaccines. The resulting polyepitopic HBV proteins as well as the recombinant T7 bacteriophage, endowed with multiple copies of the polyepitopic HBV protein constitute a prototype anti-HBV vaccine.

The invention claimed is:

1. A method of manufacturing polyepitopic protein, comprising the steps of:
   a) cloning a blunt-ended DNA sequence encoding an epitope into a DNA vector comprising two convergent DNA sequences recognized by Sap I endonuclease and a DNA sequence found between them containing a site for cloning in an insert recognised by Sma I endonuclease having a sequence selected from the group consisting of SEQ ID No: 1, 2, 3, 4, 5, 6, 7 or 11,
   b) amplifying the vector in a bacterial host, isolating the vector, digesting the vector with Sap I endonuclease, isolating a fragment containing the DNA sequence encoding the epitope,
   c) autoligating the isolated fragment of step (b),
   d) inserting the isolated fragment of step (c) into said DNA vector at a site recognised by Sap I endonuclease,
   e) transforming a bacterial host with the vector, expressing and isolating a polyepitopic protein.

2. The method according to claim 1, wherein the epitope is an HBV epitope.

3. The method according to claim 1, wherein said two convergent DNA sequences recognized by Sap I endonuclease and a DNA sequence found between them containing a site for cloning in an insert recognised by Sma I endonuclease form a monomeric unit capable of coding at least two epitopes originating from different proteins or different regions of the same protein.

4. The method according to claim 1, wherein the polyepitopic protein additionally comprise a sequence as a part thereof comprising a fusion tag containing a sequence of 6 histidine residues, and further wherein the polyepitopic protein is isolated with a metalloaffinity chromatography.

5. The method according to claim 1, wherein the step e) comprises immobilizing the polyepitopic protein on a macromolecular carrier.

6. The method according to claim 1, wherein Steps (b) to (d) are repeated to increase the size of the polyepitopic protein prior to Step (e).

7. The method according to claim 2, wherein the HBV epitope is encoded by SEQ ID NO: 9.

8. The method according to claim 3, wherein the different proteins or different regions of the same protein are encoded by a synthetic sequence.

9. The method according to claim 4, wherein the metalloaffinity chromatography comprises immobilized nickel.

10. The method according to claim 4, further comprising an additional purification step selected from the group consisting of heating the polyepitopic protein, fractionation using polyethylenimine, salting out with ammonium sulphate, and molecular sieving gel chromatography.

11. The method according to claim 5, wherein the macromolecular carrier is selected from the group consisting of microorganisms, cells, bacteria, bacteriophages, viruses, defective virions, autoaggregating proteins, and nanoparticles.

12. The method according to claim 11, wherein the macromolecular carrier is a T7 bacteriophage.

13. The method of claim 1, wherein the DNA sequence is SEQ ID NO: 7.

14. The method of claim 1, wherein the DNA vector is a protein expression vector, and additionally comprises an origin of replication, an antibiotic resistance gene, a transcription promoter, a repressor gene, and a translation initiation signal.

* * * * *